United States Patent [19]

Krbechek

[11] 4,252,730

[45] Feb. 24, 1981

[54] HYDROLYSIS OF STEROIDAL CARBAMATES

[75] Inventor: Leroy O. Krbechek, Minneapolis, Minn.

[73] Assignee: Henkel Corporation, Minneapolis, Minn.

[21] Appl. No.: 122,321

[22] Filed: Feb. 19, 1980

[51] Int. Cl.$^3$ .................................................. C07J 1/00
[52] U.S. Cl. ................................. 260/397.3; 260/397.1
[58] Field of Search ........................... 260/397.1, 397.3

[56] References Cited

U.S. PATENT DOCUMENTS 3,063,990  11/1962  Kuehne ........................... 260/239.55
3,242,168  3/1966   Mainil ............................. 260/239.5

OTHER PUBLICATIONS

Julian et al. JACS (1948) No. 3 pp. 887–892.

Primary Examiner—Elbert L. Roberts
Attorney, Agent, or Firm—Forrest L. Collins; Patrick J. Span

[57] ABSTRACT

The present invention describes a process for converting the carbamate of a steroidal amino compound to the corresponding hydrohalide.

17 Claims, No Drawings

HYDROLYSIS OF STEROIDAL CARBAMATES

BACKGROUND OF THE INVENTION

1. Field of the Art

The present invention deals with the conversion of steroids from one intermediate to another intermediate which are generally useful in the preparation of progesterone.

2. Description of the Art

It is known that progesterone and progesterone-like compounds can be made through a variety of routes. In the present invention, 20-carboxamido compounds are utilized to form progesterone and its analogs. One route utilizing an acid functionality on the steroid side chain is reported in an article entitled, "The Conversion of Hyodesoxycholic Acid to Progesterone", by Bharucha, et al, as reported in the *Canadian Journal of Chemistry*, Vol. 34, 1956 at page 982-990. The Bharucha, etal, route also utilizes N-bromosuccinimide as one of the reactants in this process. Another route utilizing an acid, this time a 20-carboxy acid of a steroid to obtain progesterone via the Oppenauer oxidation is reported by Wieland, et al, in Helvetica Chimica Acta, Vol. XXXII, Part VI (1949), No. 255 at page 1922–1933. Wieland again with his coauthor Mischler at Helvetica Chimica Acta, Vol. XXXII, Part V (1949), No. 233 at pages 1764–1769 again reports a method for obtaining progesterone through a complicated route utilizing a 20-carboxy steroid compound.

Julian, et al, in an article entitled, "Delta 20-pregnenes from Bisnor-Steroid Acids", as reported in *JACS* at Vol. LXX, published 1948, No. 3, at pages 887–892, reports that 20-carboxy steroids may be converted to useful steroids. In another article published in Helvetica Chimica Acta at Vol. XXXII, Part V (1949), No. 232 at pages 1758-1763, Meystre, et al, report that 20-carboxy steroid compounds may be converted to the corresponding chloroamine and thereafter, through a multi-step reaction, progesterone may be obtained. U.S. Pat. No. 3,519,658 issued to Adam, et al, July 7, 1970 discusses the use of N-chlorosuccinimide with steroids.

Useful steroids having a 20-carboxyl functionality are described in European Patent application No. 4-913 published Oct. 31, 1979. An additional useful product obtained therein is 3-oxo-pregna-1,4,17(20)-triene-20-carboxylic acid. More useful acids are described in U.S. Pat. No. 3,994,933 issued to Jiu, et al, Nov. 30, 1976.

To the extent that each of the foregoing references are applicable to the present invention, they are herein specifically incorporated by reference. Throughout this present invention, percentages and ratios are given by weight unless otherwise indicated, and temperatures are in degrees Celsius unless otherwise indicated.

SUMMARY OF THE INVENTION

The present invention describes a process for the hydrolytic conversion of a member selected from the group consisting of the esters of 3-oxo-pregn-4-ene-20-carbamic acid and 3-oxo-pregna-4,17(20)-diene-20-carbamic acid and mixtures thereof to the 20-amino-3-oxo-pregn-4-ene-hydrohalide and 3,20-dioxo-pregn-4-ene including the steps of:

(a) combining the carbamic acid ester with a hydrohalide acid;

(b) reacting the mixture of step (a) for a sufficient amount of time to, convert the carbamic acid ester to 20-amino-3-oxopregn-4-ene hydrohalide and 3,20-dioxo-pregn-4-ene and mixtures thereof.

DETAILED DESCRIPTION OF THE INVENTION

The present invention utilizes a steroidal acid which may be obtained according to the art. In its most practical aspect, the material is in the form of the acid or inorganic salt as the esters can cause potential side reactions and are thus not desired.

The acids which are shown in (A)–(D) below are first converted to the 20-carboxyamido derivative by reacting the acid form with sufficient amount of a halogenating agent to obtain the corresponding carbonyl halide. The carbonyl halide is thereafter reacted with a source of ammonia in a sufficient amount to form the 20-carboxyamido derivative. To conduct the first step of the reaction in order to obtain the halide it is necessary to use a halogenating agent such as thionyl chloride. It is also observed, however, that other materials may be used such as thionyl bromide, thionyl fluoride, phosphorus trichloride, phosphorus pentachloride, phosphorus pentabromide, phosphorus oxychloride, and phosphorus oxybromide.

To a large degree, however, it will be observed that the particular halogenating agent employed may depend on solvent conditions, convenience of the reaction, and tolerance of the steroid ring structure of the particular halogenating agent employed.

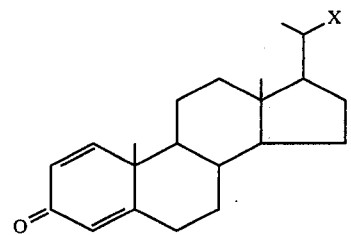

A.

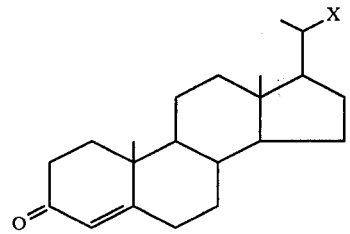

B.

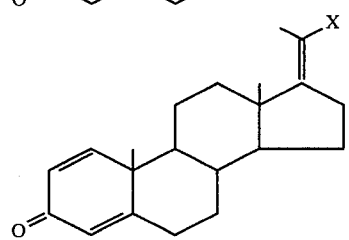

C.

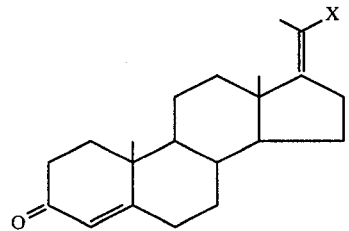

D.

In the above formulas X denotes the particular derivative. Where X is COOH the starting acid is shown. Where X is COCl, the acid halide (chloride) is shown. When X is $CONH_2$, the amide is shown and when X is NCO the isocyanate is described. The formula variable where X is N(CO)OR is the ester. When X is $NH_2$ the amine is shown and where X is $NH_2 \cdot HY$ a salt such as the hydrochloride (halide) is intended.

The second step in the reaction in obtaining the carboxyamido compound employs the use of a source of ammonia. The source of ammonia may be any material which conveniently generates ammonia under the reaction conditions specified. Convenient sources of ammonia are either ammonia itself, or a ammonium hydroxide. The equivalent amount of ammonia required to convert the carbonyl halide to the carboxyamido compound is utilized. Conveniently, however, there should be an excess amount of ammonia present only governed by the reaction conditions to avoid loss of any of the halide in the reaction.

The carboxyamido steroid as described above is then reacted with lead tetracetate to form the corresponding isocyanate. The isocyanato compound is, however, transitory inasmuch as the reaction conditions conveniently employed use an alcohol (preferably methanol) and a strong base such as sodium methoxide thereby forming the carbamate. However, where the isocyanato compounds could be isolated using related technology it is, of course, observed that the isocyanato compound could then be converted from its form as a stable intermediate to the carbamate.

The carbamate may be that corresponding to any alcohol of practical consequence in the reaction. However, it is preferred that the carbamate be selected from the group consisting of the methyl, ethyl, n-propyl, isopropyl, n-butyl, sec-butyl, and tertiary-butyl and mixtures thereof. Preferably the carbamate is either the tertiary-butyl or the methyl, most preferably the latter. The reaction to form the carbamate is best promoted by having the alcoholic base, i.e., sodium methoxide, present to catalyze the reaction.

The carbamate is then converted according to the present invention to the corresponding hydrohalide by reacting the carbamate in the presence of the hydrohalide acid for a sufficient period of time to convert the carbamate to the corresponding amino hydrohalide.

Preferably, the hydrohalide acid is selected from the group consisting of hydrochloric acid, or hydrobromic acid. It is often preferable to supercharge the system by utilizing a hydrohalide gas to provide additional driving force to complete the reaction. It is of course preferable that the hydrohalide gas correspond to the hydrohalide acid employed, i.e., where hydrochloric acid is employed, hydrogen chloride is used as the supercharging agent. The reaction may be improved by employing a cosolvent such as a halogenated hydrocarbon, i.e. methylene chloride or ethylene dichloride.

The reaction to form the hydrohalide is preferably conducted in an inert atmosphere conveniently utilizing a nitrogen blanket. The reaction is run over a considerable period of time to ensure completeness. It is often preferable to reflux the reaction mixture for a period of six or more hours to complete the reaction. It has also been discovered that the reaction proceeds at a more rapid rate due to solubility factors when a short chain organic acid is also included in the reaction mixture. Preferably the short chain organic acid is acetic acid, most preferably glacial acetic acid, as the relative strength of the acid dictates that while water may be present in the reaction mixture, the greater the acid strength the more complete the reaction. At this point, it is commented that the starting acids which are unsaturated in the A-ring at the 1–2 position should be hydrogenated as that bond is not stable under the presence of the strong acids required herein. Just as surprisingly, the 4–5 and 17–20 unsaturation are stable to the acid hydrolysis. It has been observed in the present invention that the reaction to form the hydrohalide from the carbamate of 3-oxo-pregn-4-ene-20-carboxylic acid is a very specific reaction. That is, the corresponding reactions have been attempted utilizing the carbamates of 3-oxo-pregna-1,4-diene-20-carboxylic acid and 3-oxo-pregna-1,4,17(20)-triene-20-carboxylic acid without success. In particular, it has been noted that these unsaturated steroids are subject to halogenation in the ring structure of the steroid and that it has also been observed that aromatization also occurs in the ring structure under the necessary vigorous reaction conditions to form the amino-hydrohalide of the present invention. A second point of interest is that upon hydrolysis the ester of 3-oxo-pregna-4,17(20)-diene-20-carbamic acid spontaneously rearranges in the present invention to give progesterone.

Other interesting observations when conducting the present invention are that the rate of reaction to yield the amino-hydrohalide proceeds in order of ease from the tertiary butyl to the methyl to the ethyl to the propyl and remaining butyl carbamates. That is, it is somewhat strange that the two most disrelated carbamates the methyl and tertiary butyl are the easiest to cleave to the amine. The t-butyl ester may even be cleaved with a relatively weak Lewis acids such as acetic, oxalic or mineral acids such as hydrochloric. This is in contrast to the methyl ester requiring strong acid hydrolysis. It has been observed in the present invention that when utilizing hydrobromic acid it is not particularly necessary to utilize hydrogen bromide gas in the reaction mixture whereas more vigorous thermal action is needed when hydrochloric acid is utilized without hydrogen chloride gas being present. In general, however, the reaction proceeds at from 10° C. to over 100° C.

The following are examples of the present invention.

EXAMPLE I

The hydrochloride of 20-amino-3-oxo-pregn-4-ene is obtained by reacting 5.0 grams of the methyl carbamate of 20-amino-3-oxo-pregn-4-ene with 80 ml. of concentrated hydrochloric acid which has been saturated with anhydrous hydrogen chloride. The system is refluxed for a period of greater than six hours under a nitrogen atmosphere. The acid is then removed at reduced pressure after which the residue is dissolved in methylene chloride. The methylene chloride solution was washed twice with a saturated salt solution and dried over magnesium sulfate. Thereafter, the reaction mixture was stripped to dryness to leave the hydrochloride of 20-amino-3-oxo-pregn-4ene.

The above reaction can be utilized to increase the yield by adding 80 ml. of glacial acetic acid to the reaction mixture in the first instance. The overall yield is observed to be greater than 90% with very little unreacted carbamate remaining. Another alternative of the present invention is where the anhydrous hydrogen chloride is omitted, the reaction must be conducted for a greater period of time in order to obtain the same yields.

The present example is again conducted, this time utilizing concentrated hydrobromic acid and omitting the acetic acid as well as anhydrous hydrogen bromide. The system was again under nitrogen blanket and following the above procedure other than as indicated herein the yield will be observed to be on the order of that previously reported.

The above example is repeated using the t-butyl ester with similar results. The methyl carbamate of 3-oxo-pregna-4,17(20)-diene is converted to progesterone through the acid hydrolysis route described above. Where the methyl ester of 3-oxo-pregna-1,4,17(20)-triene-20-carbamic acid or the 3-oxo-pregna-1,4-diene-20-carbamic acid ester is employed, the desired product is not obtained.

What is claimed is:

1. A process for the hydrolytic conversion of a member selected from the group consisting of the esters of 3-oxo-pregn-4-ene-20-carbamic acid and 3-oxo-pregna-4,17(20)-diene-20-carbamic acid and mixtures thereof to the 20-amino-3-oxo-pregn-4-ene-hydrohalide and 3,20-dioxo-pregn-4-ene including the steps of:
   (a) combining the carbamic acid ester with a hydrohalide acid;
   (b) reacting the mixture of step (a) for a sufficient amount of time to,
convert the carbamic acid ester to 20-amino-3-oxo-pregn-4-ene hydrohalide and 3,20-dioxo-pregn-4-ene and mixtures thereof.

2. The process of claim 1 wherein the hydrohalide acid is the concentrated form of the acid.

3. The process of claim 1 additionally containing a hydrohalide gas saturated in the hydrohalide acid.

4. The process of claim 1 conducted in the presence of an inert atmosphere.

5. The process of claim 1 wherein the hydrohalide acid is hydrochloric acid.

6. The process of claim 3 wherein the hydrohalide gas is hydrogen chloride.

7. The process of claim 3 wherein the hydrohalide gas and the hydrohalide acid are hydrogen chloride and hydrochloric acid.

8. The process of claim 4 wherein the inert atmosphere is nitrogen.

9. The process of claim 6 wherein the reaction mixture is refluxed for 6 or more hours.

10. The process of claim 1 containing as an additional ingredient a short chain organic acid.

11. The process of claim 1 wherein the hydrohalide acid is hydrobromic acid.

12. The process of claim 10 wherein the acid is glacial acetic acid.

13. The process of claim 1 wherein the carbamic acid ester is selected from the group consisting of methyl, ethyl, propyl, isopropyl, n-butyl, sec-butyl, and the tertiary-butyl and mixtures thereof.

14. The process of claim 1 wherein the carbamic acid ester is the methyl ester.

15. The process of claim 13 wherein the carbamic acid ester is tertiary-butyl.

16. The process of claim 1 wherein the amino hydrohalide is dissolved in methylene chloride, washed with saturated sodium chloride, dried over magnesium sulfate, filtered and any solvent present stripped off to yield the substantially pure amino hydrohalide.

17. A process for the hydrolytic conversion of the tertiary butyl ester of a member selected from the group consisting of 3-oxo-pregn-4-ene-20-carbamic acid and 3-oxo-pregna-4,17(20)-diene-20-carbamic acid and mixtures thereof including:
   (a) contacting the carbamic acid ester with a Lewis acid;
   (b) reacting the mixture of (a) for a sufficient time to generate 20-amino-3-oxo-pregn-4-ene and 3,20-dioxo-pregn-4-ene and mixtures thereof.

* * * * *